(12) United States Patent
Kroll-Orywahl et al.

(10) Patent No.: US 9,014,824 B2
(45) Date of Patent: Apr. 21, 2015

(54) BANDAGE AND ELECTRODE SYSTEM

(75) Inventors: Olaf Kroll-Orywahl, Göttingen (DE);
Holger Reinhardt, Kempen (DE); Erik Albrecht-Laatsch, Göttingen (DE)

(73) Assignee: Otto Bock Healthcare GmbH, Duderstadt (DE)

( * ) Notice: Subject to any disclaimer, the term of this patent is extended or adjusted under 35 U.S.C. 154(b) by 0 days.

(21) Appl. No.: 14/111,997

(22) PCT Filed: Apr. 11, 2012

(86) PCT No.: PCT/EP2012/001566
§ 371 (c)(1),
(2), (4) Date: Oct. 15, 2013

(87) PCT Pub. No.: WO2012/143100
PCT Pub. Date: Oct. 26, 2012

(65) Prior Publication Data
US 2014/0039595 A1     Feb. 6, 2014

(30) Foreign Application Priority Data

Apr. 18, 2011   (DE) .......................... 10 2011 018 470

(51) Int. Cl.
| A61N 1/00 | (2006.01) |
| A61B 5/04 | (2006.01) |
| A61N 1/04 | (2006.01) |
| A61F 5/02 | (2006.01) |
| A61N 1/32 | (2006.01) |
| A61N 1/36 | (2006.01) |
| A61N 1/22 | (2006.01) |

(52) U.S. Cl.
CPC .............. *A61N 1/0452* (2013.01); *A61F 5/028* (2013.01); *A61N 1/0476* (2013.01); *A61N 1/0484* (2013.01); *A61N 1/0492* (2013.01); *A61N 1/321* (2013.01); *A61N 1/36003* (2013.01); *A61N 1/36014* (2013.01); *A61N 1/22* (2013.01)

(58) Field of Classification Search
USPC ............................................ 607/149; 600/372
See application file for complete search history.

(56) References Cited

U.S. PATENT DOCUMENTS

| 4,445,518 | A | 5/1984 | Eggli et al. |
| 2002/0128686 | A1 | 9/2002 | Minogue et al. |
| 2003/0114892 | A1* | 6/2003 | Nathan et al. ................... 607/48 |
| 2008/0045872 | A1 | 2/2008 | Bauerfeind et al. |
| 2010/0004715 | A1 | 1/2010 | Fahey |

FOREIGN PATENT DOCUMENTS

| CN | 201625339 U | 11/2010 |
| DE | 102004009210 A1 | 9/2005 |
| EP | 0948972 A2 | 10/1999 |
| GB | 342419 | 2/1931 |
| GB | 2400915 A | 10/2004 |

OTHER PUBLICATIONS

PCT International Search Report for PCT International Patent Application No. PCT/EP2012/001566, mailed Jul. 4, 2012.

* cited by examiner

*Primary Examiner* — Nicole F Lavert
(74) *Attorney, Agent, or Firm* — Holland & Hart

(57) ABSTRACT

A bandage having at least one support element and at least two electrodes that are spaced apart from one another, characterized in that at least two pads that are finable with a fluid are arranged on the at least one support element, and at least one electrode is fastened to each pad, wherein the at least two pads are connected to each other via at least one fluid connection in such a manner that an internal pressure compensation can take place between at least two of the pads.

20 Claims, 4 Drawing Sheets

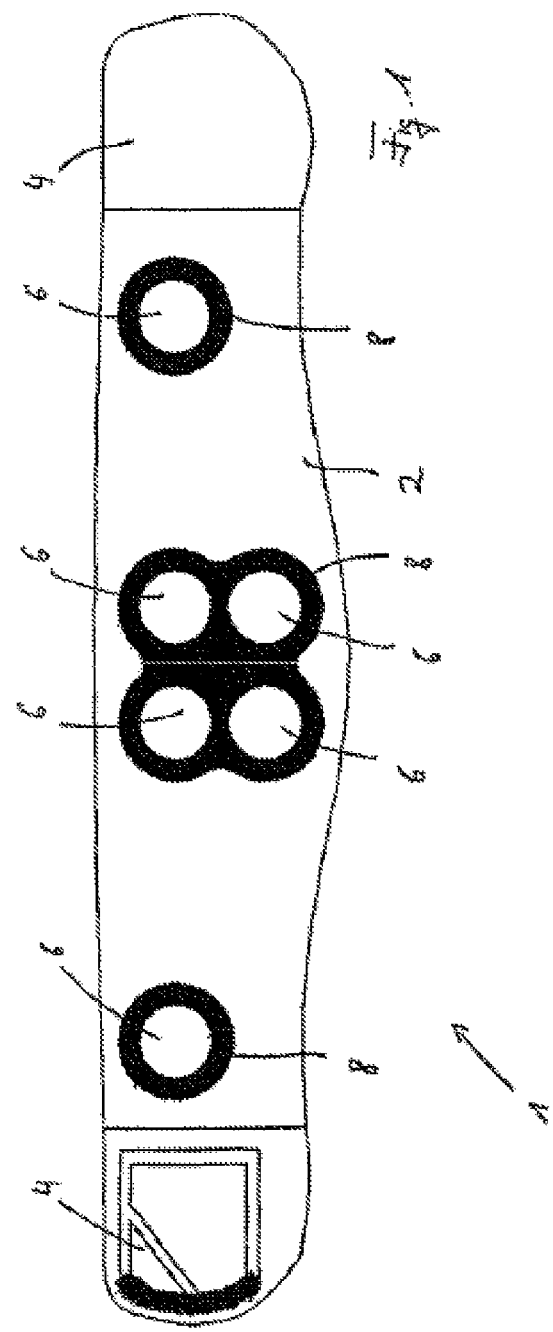

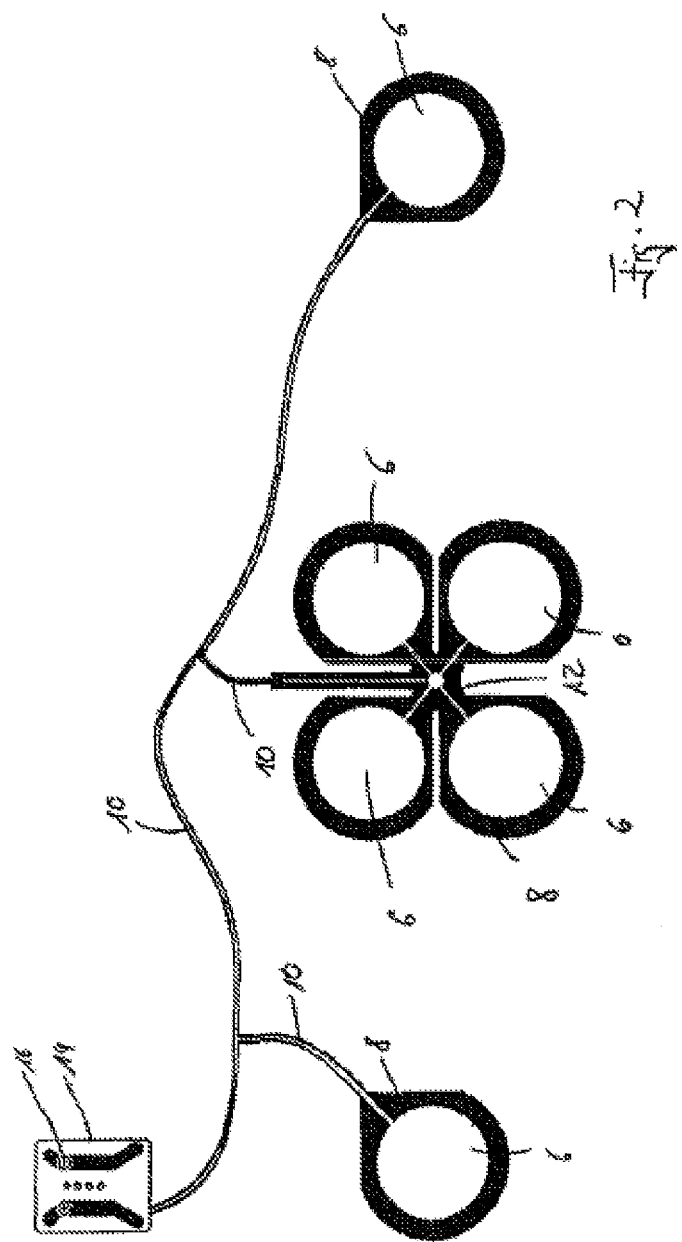

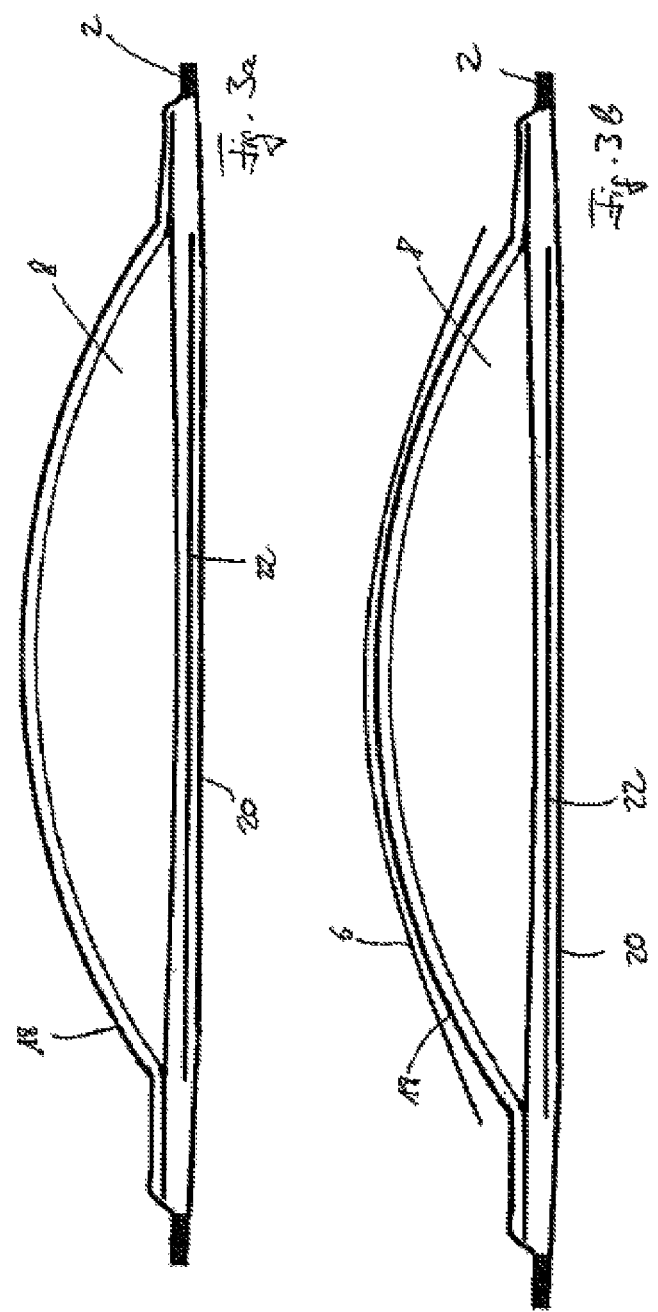

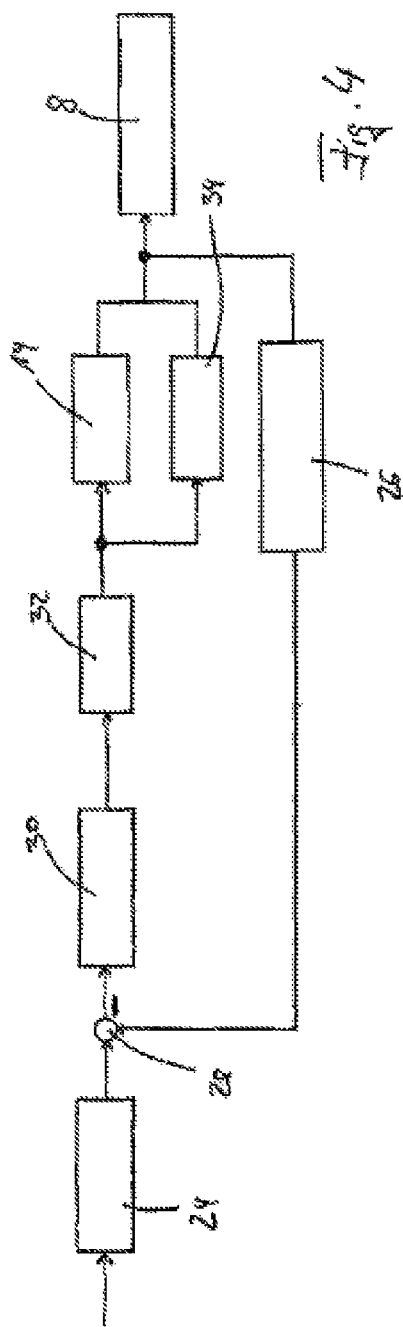

BANDAGE AND ELECTRODE SYSTEM

TECHNICAL FIELD

The invention relates to a bandage having at least one carrier element and at least two spaced-apart electrodes. The invention also relates to an electrode system for such a bandage.

BACKGROUND

Such a bandage is known, for example, from DE 10 2004 009 210 A1. The at least one carrier element, in this case, is an elastic belt which can be positioned, for example, around a patient's body. However, it is also possible for the at least one carrier element to be configured in other forms, as is known, for example, for knee orthoses, lower-leg orthoses or other bandage systems.

Such systems are often nowadays provided with electrodes, in order to allow electrotherapeutic currents to penetrate into the human body and thus stimulate muscle growth and muscle training.

In order to achieve an optimum effect here, it is important for electrical contact to be established between the electrode and the skin of the person wearing the bandage. The fact that the person wearing the bandage system or the bandage is constantly moving proves to be problematic here. It is precisely in the rehabilitation phase following an injury or illness that it is fundamentally important for the patient to be active. If the electrical stimulation or electrical therapy is to be successful, permanent contact of the electrodes as the muscles are moving is important even in these conditions.

If, as the person wearing the bandage is moving, the electrode slips such that the contact surface area with the human skin is reduced, this results, with the same amount of current being introduced into the body, in considerably higher current densities on account of the contact surface area now being smaller. This can result in local burning. The same applies if the person wearing the bandage begins to sweat under the electrode. This considerably increases the conductivity, that is to say the electrical contact between the electrode and the human skin, and therefore, with the same voltage, there is a local increase in current.

US 2002/0128686 A1, now issued as U.S. Pat. No. 7,069,089, discloses an apparatus for stimulating a patient's abdominal muscles. Various electrodes are arranged on the patient's skin here. In order to achieve particularly good electrical contact, that side of the electrode which is directed toward the patient is provided with an electrically conductive coating, for example in the form of a gel. These so-called gel electrodes, which stick to the patient's skin, have the disadvantage of possibly causing skin irritations and of forming folds, which may result, in turn, in undesired electrical voltage peaks, which in some cases give rise to burning. In addition, it is unpleasant for the wearer to wear the electrodes sticking to his body over a relatively long period of time.

US 2010/0004715 A1, now issued as U.S. Pat. No. 8,285,381, discloses an electrical-therapy apparatus which has at least one electrode which can stimulate muscle contractions. The apparatus described in said document also has sensors which pick up, and pass on to a control unit, signals which are emitted from the electrically stimulated muscle groups as a response to the electrical stimulation. This is intended to optimize the position and the effect of the electrodes, and malfunctioning of the electrodes, for example overheating, should be quick to detect. This is advantageous, in particular, for patients who are comatose, sedated or otherwise incapable of communicating with their surroundings.

EP 0 948 972 A2 discloses a device which allows a defibrillator to be worn on the patient's body by means of a plurality of belts or straps. It is possible here for the electrodes to be arranged in elastic pockets, which may consist, for example, of an electrical non-conductive woven fabric. This avoids direct contact between the electrode and the wearer's skin. If, then, relevant sensors establish that current has to be introduced through the electrodes into the patient's body, use is made of an electrically conductive gel which passes out of the electrode and can pass easily through the woven fabric. This ensures electrical contact at any time. This process is only possible, however, if, as in the case of a defibrillator, current shocks have to be introduced into the patient's body in exceptional cases, and only over a very short period of time. This solution cannot be used for the electrical stimulation of muscles, which has to take place over a relatively long period of time.

In order to ensure that, even as a person wearing the bandage is moving, the electrodes do not move relative to the skin, it is necessary to have contact pressure of the electrodes against the wearer's skin in a certain region. This is difficult, in particular, when the person wearing the bandage, for example as he is sitting, leans against the backrest of a chair or bends forward, in which case there is no longer any contact with the backrest. In both cases, the contact pressure of the electrode against the skin of the person wearing the bandage changes, and therefore the electrical contact, in particular the electrical conductivity of the connection between the electrode and the skin, is changed considerably.

For this purpose, DE 10 2004 009 210 A1 proposes to fit the electrodes on an elastic bandage. A pocket is intended to be arranged on the elastic bandage, in the region of the electrodes, said pocket consisting of a material which is significantly more non-elastic than the bandage. The pocket made of the non-elastic material contains an elastic pad, which may be designed, for example, in the form of an inflatable tube. If said tube is then inflated, the pocket, on account of being largely non-elastic, can expand only in the direction of the electrode and thus presses the latter to a more pronounced extent against the patient's skin.

It is disadvantageous that, for the electrodes, a non-elastic pocket has to be arranged on the otherwise elastic bandage. This means that the task of positioning the electrodes is no longer a flexible one, rather, the position at which electrodes may be provided on the bandage is already defined by the manufacturer. In addition, a separate component has to be arranged on the bandage, and this increases the outlay in terms of production and costs.

It is also disadvantageous that, although it is possible, by way of the degree of filling of the inflatable tube, to set the pressure by which the electrode is pressed onto the patient's skin, said pressure, however, can change to a pronounced extent, for example, when the patient is moving. In particular it is possible for the pressure at some electrodes to increase to a pronounced extent as a result of the patient moving or leaning against an object, for example a backrest of a chair, whereas it drops considerably at other electrodes. It is not possible for the solution proposed in the prior art to make allowances for this different pressure development at different electrodes.

SUMMARY

It is therefore an object of the invention to improve a bandage of the type in question such that the positioning of the electrodes on the at least one carrier element can take place in a flexible manner and allowances can readily be made for the different pressure development at different electrodes.

The invention achieves the set object by way of a bandage of the generic type which is distinguished in that at least two fluid-fillable pads are arranged on the at least one carrier element, and at least one electrode is fastened on each pad, wherein the at least two pads are connected to one another via at least one fluid connection so as to allow internal-pressure equalization between at least two of the pads.

Consequently at least two fluid-fillable, for example inflatable, pads are located on the at least one bandage-carrier element, which may be, for example, a belt. At least one electrode is located on a side of each pad which is directed away from the carrier element. Consequently different pads are located between the at least two spaced-apart electrodes and the at least one carrier element. These pads are connected to one another via at least one fluid connection so as to allow equalization of the internal pressures in the two pads. This ensures that the same pressure prevails in each of the pads at any one time, since pressure equalization takes place between the pressure pads. The same pressure thus naturally also prevails in the fluid connection. Even if one or more of the pads are subjected to relatively pronounced loading as a result of the patient moving or leaning against something, the pressure is not just locally applied to this electrode; rather, pressure equalization by way of the at least one fluid connection also provides for pressure to be transmitted to all the other pads. Particular loading of one or more of the electrodes, or of the pads located thereon, is usually accompanied by pressure being relieved from other electrodes arranged on the at least one carrier element. It is thus usually the case, for example with a back bandage, when the patient leans against the backrest of a chair, that the electrodes which are located in the region of the patient's back are subjected to pronounced pressure, whereas the electrodes which are arranged in the region of the patient's stomach are relieved of loading to a considerable extent. The connection of the various pads via the at least one fluid connection here allows for pressure equalization, and therefore all the electrodes are subjected to equal loading and are pressed against the patient's skin.

Configuring a bandage according to the invention additionally makes it possible to do away with the prior-art pockets made of an essentially non-elastic material. This not only reduces the outlay in terms of design and costs, but, at the same time, considerably increases the flexibility for positioning the electrodes. It is thus possible for the electrodes, with a pad already fastened thereon, to be fastened freely on the at least one carrier element of the bandage, for example, via touch-and-close fasteners, snap fasteners or the like. This makes it possible to use the same bandage for stimulating different muscle groups. In addition, it is also the case that there is no restriction to the elasticity of the bandage in the region of the electrodes.

It is possible here for the electrodes to be designed not just for transmitting electrical pulses into the body. The electrodes may also be in the form of EMG electrodes (EMG=electromyogram), which can pick up signals from the body. It is also conceivable to have a combination of different electrodes on a bandage and in an electrode system.

In a particularly advantageous configuration, precisely one electrode is arranged on each pad. As an alternative to this, it is also possible to provide relatively large pads on which more than one electrode is arranged. This is expedient, in particular, when a plurality of electrodes are to be arranged very closely to one another on the body of the person wearing the bandage. As soon as the electrodes are spaced apart from one another, however, it is recommended to provide a separate pad for each electrode. This means that in particular the quantity of fluid which is introduced into the pads can be reduced to a considerable extent, which is advantageous, in particular, when the pads are filled not with air, but, for example, with a special fluid. The bandage preferably comprises a pump, which is intended to pump the fluid into the pads and/or out of the pads. It is thus possible for the degree of filling of the pads to be adapted individually to each case. The pump can preferably be operated electrically. The degree of filling can be controlled particularly straightforwardly as a result. If the electrodes are provided, for example, for locations at which there is normally a certain distance between the patient's skin and the bandage applied, the pads can be filled to a relatively pronounced extent, in which case they achieve a relatively large degree of expansion and press the electrodes, over the distance present, against the patient's skin so as to ensure optimum contact. If the electrodes, in contrast, are provided for locations which butt directly against a bandage applied, a less pronounced degree of filling is sufficient, and therefore some of the fluid which is still located in the pads can be drained or pumped out.

In a preferred configuration, there is at least one sensor provided for measuring the internal pressure. Such a sensor may be arranged, for example, in one of the pads, in the at least one fluid connection or in the pump. Any positioning which makes it possible to determine the internal pressure prevailing in the pads possible. The bandage then preferably also comprises an electrical control means, which is intended to control the pump in dependence on the values measured for the internal pressure. It is thus possible for the internal pressure of the fluid in the pads to be adapted and readjusted even while the bandage is being worn for example over a relatively long period of time. This ensures that the desired pressure always prevails. If, for example, the person wearing a bandage leans against the backrest of a chair, the pressure to which the electrode is subjected in this region is increased to a pronounced extent. This increases overall the pressure in the system made up of the pads and of the at least one fluid connection, and therefore it may be advantageous for some of the fluid to be pumped out of the pads and/or the fluid connection. This further reduces the pressure, in which case the pre-set desired pressure can be achieved. As an alternative, it may also be advantageous, while the bandage is being worn, for an additional amount of fluid to be pumped into the system made up of pads and of at least one fluid connection, in order for the pressure to be increased again, for example if the bandage and/or the electrodes slip such that the pressure in the pads, and thus also the contact pressure of the electrode against the skin of the person wearing the bandage, decreases. This is readily possible by way of the electrical control means, in which case always the optimum pressure can be adjusted.

It has been found to be advantageous if a plate element is provided between at least one pad and the at least one carrier element, said plate element having a lower level of elasticity than the carrier element. As a result, in particular in the case of very elastic carrier elements, for example elastic bandages or belts, the active pumping up of the pads with the fluid cannot lead to the pad being able to expand in the direction away from the electrode. The plate element, with its low level of elasticity, forces the pad to expand in the direction of the electrode, and therefore the electrode is pressed to a more pronounced extent in the direction of the patient. The plate element provided thus performs the task of the essentially non-elastic pocket from the prior art. The advantage here, however, is that the plate element here is provided between the pad and the at least one carrier element, and therefore it does not adversely affect the flexibility for selecting the position of electrodes on the at least one carrier element.

As an alternative to this, it is also possible for no plate element to be used, in which case the pads can protrude freely in both directions.

Each of the pads can be made up of a plurality of sheet-material elements. These can be connected to one another, for example, by means of ultrasonic welding, which is known, for example, from air-mattress production, or by means of adhesive bonding. As an alternative, it is also possible, of course, to use friction welding, laser methods or high-frequency welding. It is preferably possible for the electrodes, on a side which is directed away from the pad, to have an adhesive-bonding layer for sticking to a patient's skin. This can further improve the contact.

An electrode system according to the invention has at least two electrodes and at least two pads, wherein at least one electrode is arranged on each pad. In addition, the pads are connected to one another via at least one fluid connection so as to allow internal-pressure equalization between at least two of the pads. A plate element is provided on preferably at least one pad, on a side directed away from the electrode arranged thereon.

In addition, it is preferably the case both for an electrode system and for a bandage that a fastening means, for example a touch-and-close fastener, is provided on each pad, on the side directed away from the electrodes, and allows the electrode system to be fastened on a belt or a bandage. This makes it possible for a conventional bandage, on which the manufacturer has not provided any electrodes, to be retrofitted with electrodes. As the individual pads, and the electrodes arranged thereon, are fitted in a flexible manner, they can be used for stimulating a wide variety of different muscle groups. In particular it is possible for the electrode system, once the stimulation therapy has ended, to be removed from the belt or the bandage and used with another bandage for other muscle groups. This means that the electrode system is recyclable, in which case it is not necessary for a new custom-made bandage to be produced for each illness, or possibly even for each patient, for example in a hospital or in a rehabilitation clinic. The treatment costs therefore decrease considerably.

An in particular electrical control means both controls the electrodes via which electrical pulses should be emitted to the body and further processes the electrical signals picked up by EMG electrodes. In a preferred embodiment, the electrical control means is arranged in a housing which encloses the pump. It is thus possible for the person wearing the bandage here both to make adjustments to the pump, and thus to the filling pressure of the pads, and to control, for example, the sequence of electrical pulses emitted. All that is required, in this configuration, is for just one component, that is to say the combined housing for the pump and the control means, to be arranged externally on the bandage.

BRIEF DESCRIPTION OF THE DRAWINGS

An exemplary embodiment of the present invention will be explained in more detail hereinbelow with the aid of a drawing, in which:

FIG. 1 shows a schematic plan view of a bandage according to a first exemplary embodiment of the present invention, FIG. 2 shows the schematic illustration of an electrode system according to an exemplary embodiment of the present invention, FIG. 3a shows a schematic cross section through a carrier element in the region of a pad, FIG. 3b shows the illustration from FIG. 3a with an electrode arranged thereon, and FIG. 4 shows a plan of operation for regulating the internal pressure in the pads.

DETAILED DESCRIPTION

FIG. 1 shows the schematic plan view of a bandage 1 according to a first exemplary embodiment of the present invention. Said bandage 1 has a carrier element 2 which, in the exemplary embodiment shown in FIG. 1, is in the form of a belt. Closing elements 4, which may be designed, for example, as the two parts of a touch-and-close fastener, are located at the right-hand and left-hand ends of the carrier element 2. As an alternative, of course, buckles, snap fasteners and the like are also conceivable here.

The bandage 1 shown in FIG. 1 has six electrodes 6, each arranged on a pad 8. The pads 8 are arranged on the carrier element 2, which in this case is in the form of a belt. Other configurations of the carrier element 2 are also conceivable. The only important factor for the invention is that the bandage 1 has at least one carrier element 2, on which the pads 8 are arranged.

The view shown in FIG. 1 thus shows that side of the bandage 1 which is directed toward the patient's body. The respectively right-hand and left-hand electrodes 6 are arranged on a separate pad 8, whereas the four electrodes 6 arranged in the central region of the carrier element 2 rest on a common pad 8. The pads 8 are connected to one another by fluid connections (not shown), and this therefore always allows equalization of the internal pressure in the different pads 8. Such a fluid connection may be formed, for example, by a tube 10 or a channel. The pads can also be connected by a sheet material welded in an air-tight manner.

FIG. 2 shows a schematic illustration of an electrode system with electrodes 6 and the pads 8 located therebeneath. Each of the pads 8 has a cavity which can be filled with a fluid. These cavities are congruent with the electrodes 6 in FIG. 2. The various pads 8 are connected to one another via a plurality of tubes 10, which form the fluid connection in the exemplary embodiment shown. The common pad 8 for the four electrodes 6 arranged in the central region of the bandage 1 shown in FIG. 1 has four fluid-fillable chambers. The latter are connected to one another within the pad 8 via a cross-shaped connection 12 and therefore internal-pressure equalization can also take place here.

A schematically illustrated pump 14 is connected to the connecting tube 10. Said pump additionally comprises an electrical control means 16, which is intended to control the pump 14. This pump makes it possible both to pump a medium through the tubes 10 and into the pads 8 and to drain medium out of the pads 8. It is thus possible for the internal pressure, and thus also the contact pressure of the electrodes against the wearer's body, to be set individually.

FIG. 3a shows a section through a carrier element 2 in the region of a pad 8. In the exemplary embodiment shown in FIGS. 3a and 3b, the pad 8 is integrated in the carrier element 2. It can be seen that is arranged between an inner wall 18, which is directed toward the patient, and an outer wall 20, which is located on the opposite side. This ensures that the pad 8 cannot slip relative to the carrier element 2. As an alternative to this, it is also possible for fastening elements, for example a touch-and-close fastener or the like, to arrange the pad 8 on that side of the carrier element which is directed toward the patient. In this case, the flexibility for positioning the pads 8, and thus also the electrodes 6, which are to be arranged on the pads 8, is increased to a considerable extent. There is a risk, however, of the pad 8, and thus also the electrode 6, becoming detached from the carrier element 2 and being capable of being displaced relative to the same.

A plate element 22 is illustrated schematically between the pad 8 and the outer wall 20 of the carrier element 2. As shown in FIGS. 3*a* and 3*b*, said plate element 22 effectively prevents the pad 8 from expanding in the direction of the outer wall 20 of the carrier element 2 even when it is filled with the fluid, for example air.

FIG. 3*b* shows the situation from FIG. 3*a* with an electrode 6 arranged on the inner wall 18 of the carrier element 2. It can be seen that inflation of the pad 8, or pumping the fluid into the pad 8, results in expansion of the pad 8 only in the direction of the inner wall 18 of the carrier element 2. The electrode 6 arranged on this side is thus pressed in the direction of the patient or the person wearing the bandage 1, and this therefore gives rise to optimum contact with the wearer's skin. This ensures that the contact surface area remains constant over time and is not increased or reduced as a result of the electrodes slipping, being displaced or becoming detached. It is therefore certain that the optimum current pulses and signals penetrate into the body of the person wearing the bandage 1 and muscle stimulation can thus take place in the best manner possible.

In the exemplary embodiment shown in FIG. 3*b*, the electrode 6 is fastened on the inner wall 18 of the carrier element 2, for example, via adhesive-bonding spots, touch-and-close fasteners or similar fastening means. As an alternative to this, it is also possible for the electrode 6 to be fastened directly on the pad 8, if the latter is arranged on that side of the inner wall 18 of the carrier element 2 which is directed toward the person wearing the bandage 1. The combination made up of the pad 8 and electrode 6 is thus easy to shift relative to the carrier element 2, and therefore the same bandage 1 can be used in order to stimulate different muscle groups in different parts of the human body.

FIG. 4 shows, schematically, a plan of operation for controlling the internal pressure in the air chambers. Starting from the left, a target variable 24, corresponding to the desired internal pressure in the air chambers of the pads 8, is predetermined. The pads 8 are located at the far right-hand end of the plan of operation. The internal pressure is measured immediately upstream of the pads 8 by a sensor 26, which has not been shown in any of the previous figures and may be arranged, for example, directly in one of the pads 8 or in the pump 14. Said internal pressure is compared, in a comparator 28, with the target variable 24, that is to say the desired internal pressure. If there are any deviations here, a regulating element 30 and an actuator 32 activate a control element, in order to change the internal pressure in the pads 8 which has been measured by the sensor 26. Said control element may be, on the one hand, the pump 14, which is illustrated schematically in the figure, or else a valve 34. If the internal pressure in the pads 8 which has been measured by the sensor 26 is too large in relation to the desired internal pressure provided as target variable 24, some of the fluid located in the pads 8 is drained via the valve 34. The internal pressure thus decreases and comes more into line with the desired target variable 24. However, if the internal pressure which has been measured by the sensor 26 is smaller than the internal pressure predetermined as the target variable 24, the internal pressure in the pads 8 is increased via the pump 14 by fluid being pumped into the pads 8.

LIST OF DESIGNATIONS

1 Bandage
2 Carrier element
4 Closing element
6 Electrode
8 Pad
10 Tube
12 Connection
14 Pump
16 Electrical control means
18 Inner wall
20 Outer wall
22 Plate element
24 Target variable
26 Sensor
28 Comparator
30 Regulating element
32 Actuator
34 Valve

The invention claimed is:

1. A bandage, comprising:
   at least one carrier element;
   at least two spaced-apart electrodes;
   at least two fluid-fillable pads arranged on the at least one carrier element;
   at least one electrode fastened on each of the at least two fluid-fillable pads;
   wherein the at least two fluid-fillable pads are connected to one another via at least one fluid connection so as to allow internal-pressure equalization between at least two of the fluid-fillable pads.

2. The bandage as claimed in claim 1, wherein precisely one electrode is arranged on each of the at least two fluid-fillable pads.

3. The bandage as claimed in claim 1, further comprising a pump, which is intended to pump the fluid into the at least two fluid-fillable pads and/or out of the at least two fluid-fillable pads.

4. The bandage as claimed in claim 3, wherein the pump can be operated electrically.

5. The bandage as claimed in claim 1, further comprising at least one sensor provided for measuring an internal pressure.

6. The bandage as claimed in claim 5, further comprising an electrical control means, which is intended to control the pump in dependence on the values measured for the internal pressure.

7. The bandage as claimed in claim 1, wherein a plate element is provided between at least one of the at least two fluid-fillable pads and the at least one carrier element, said plate element having a lower level of elasticity than the carrier element.

8. The bandage as claimed in claim 1, wherein each of the at least two fluid-fillable pads is made up of a plurality of sheet-material elements.

9. The bandage as claimed in claim 3, wherein a housing which encloses the pump contains a control device, which is intended to activate the electrodes such that predetermined electrical signals are emitted or signals picked up by the electrodes can be subjected to further processing.

10. The bandage as claimed in claim 1, wherein a fastening element, for example an element of a touch-and-close fastener, is arranged on the pads, and allows the pads to be positioned freely on the carrier element.

11. An electrode system for a bandage as claimed in claim 1, having at least two electrodes, and having at least two fluid-fillable pads, wherein at least one electrode is arranged on each pad, and wherein the pads are connected to one another via at least one fluid connection so as to allow internal-pressure equalization between the at least two pads.

12. The electrode system as claimed in claim 11, wherein a plate element is provided on at least one pad, on a side which is directed away from the electrode arranged thereon.

13. A bandage, comprising:
at least one carrier element;
at least two spaced-apart electrodes;
at least two fluid-fillable pads arranged on the at least one carrier element;
at least one electrode positioned on each fluid-fillable pad;
at least one fluid connection configured to connect the at least two fluid-fillable pads to one another to allow internal-pressure equalization between two or more of the at least two fluid-fillable pads.

14. The bandage as claimed in claim 13, wherein only one electrode is arranged on each fluid-fillable pad.

15. The bandage as claimed in claim 13, further comprising a pump configured to deliver fluid into or out of the at least two fluid-fillable pads.

16. The bandage as claimed in claim 15, wherein the pump is operated electrically.

17. The bandage as claimed in claim 13, further comprising at least one sensor provided for measuring an internal pressure of the at least two fluid-fillable pads.

18. The bandage as claimed in claim 17, further comprising an electrical controller configured to control the pump in response to the measured internal pressure.

19. The bandage as claimed in claim 13, further comprising a plate element provided between the at least one pad and the at least one carrier element, the plate element having a lower level of elasticity than the at least one carrier element.

20. The bandage as claimed in claim 15, further comprising a housing configured to encloses the pump, and a control device configured to activate the at least two electrodes such that predetermined electrical signals are emitted or signals picked up by the at least two electrodes are subjected to further processing.

* * * * *